United States Patent
Collier et al.

(10) Patent No.: US 10,358,710 B2
(45) Date of Patent: Jul. 23, 2019

(54) WEAR RESISTANT COATING

(71) Applicant: BRENCO SURFACE ENGINEERING PTY LTD, Canning Vale, Western Australia (AU)

(72) Inventors: Sean Collier, Canning Vale (AU); Steve Reynolds, Canning Vale (AU)

(73) Assignee: Brenco Surface Engineering Pty Ltd., Canning Vale, Western Australia (AU)

(*) Notice: Subject to any disclaimer, the term of this patent is extended or adjusted under 35 U.S.C. 154(b) by 34 days.

(21) Appl. No.: 15/223,540

(22) Filed: Jul. 29, 2016

(65) Prior Publication Data
US 2018/0030585 A1    Feb. 1, 2018

(51) Int. Cl.
*C23C 4/123* (2016.01)
*A61L 2/07* (2006.01)
(Continued)

(52) U.S. Cl.
CPC ............. *C23C 4/123* (2016.01); *A61L 2/07* (2013.01); *B23K 9/04* (2013.01); *B23K 9/167* (2013.01);
(Continued)

(58) Field of Classification Search
None
See application file for complete search history.

(56) References Cited

U.S. PATENT DOCUMENTS 4,299,860 A * 11/1981 Schaefer .............. B23K 35/327
                                                           148/525
4,434,189 A     2/1984 Zaplatynsky
(Continued)

FOREIGN PATENT DOCUMENTS

CN    202152365 U    2/2012
CN    104372335 A    2/2015
(Continued)

OTHER PUBLICATIONS

Great Britain Combined Search and Examination Report for corresponding Great Britain Patent Application No. GB1712250.8, dated Dec. 22, 2017, 8 pages.
(Continued)

*Primary Examiner* — Nathan T Leong
(74) *Attorney, Agent, or Firm* — Merchant & Gould P.C.

(57) ABSTRACT

A method of forming a wear resistant and galling resistant coating for abrasive environments and a feed material for the method are disclosed. The feed material is for forming a wear resistant and galling resistant coating on a substrate by a welding process that heats the feed and the substrate. The feed material comprises 35 to 50 wt % titanium nitride particles and a balance of commercially pure titanium or titanium alloy particles and incidental impurities. The method involves delivering the feed material to a surface of a substrate and exposing the feed material and the substrate to sufficient energy to cause at least the commercially pure titanium or titanium alloy particles in the feed to melt and at least some of the titanium nitride particles in the feed to melt, thereby forming a melt pool. On solidification of the melt pool, at least some of the titanium nitride particles are embedded in a matrix formed from melt pool, thereby forming a wear resistant and galling resistant coating on the substrate. A wear resistant and galling resistant coating formed of the feed material is also disclosed.

15 Claims, 3 Drawing Sheets

(51) Int. Cl.

| | |
|---|---|
| *C23C 4/02* | (2006.01) |
| *C23C 4/06* | (2016.01) |
| *B23K 9/04* | (2006.01) |
| *B23K 9/167* | (2006.01) |
| *B23K 9/173* | (2006.01) |
| *B23K 9/23* | (2006.01) |
| *B23K 10/02* | (2006.01) |
| *B23K 26/00* | (2014.01) |
| *B23K 26/08* | (2014.01) |
| *B23K 26/14* | (2014.01) |
| *B23K 26/34* | (2014.01) |
| *C23C 24/08* | (2006.01) |
| *C23C 24/10* | (2006.01) |
| *C23C 26/02* | (2006.01) |
| *B23K 26/144* | (2014.01) |
| *B23K 101/04* | (2006.01) |
| *B23K 103/14* | (2006.01) |

(52) U.S. Cl.
CPC .............. *B23K 9/173* (2013.01); *B23K 9/23* (2013.01); *B23K 10/027* (2013.01); *B23K 26/0006* (2013.01); *B23K 26/08* (2013.01); *B23K 26/144* (2015.10); *B23K 26/1476* (2013.01); *B23K 26/34* (2013.01); *C23C 4/02* (2013.01); *C23C 4/06* (2013.01); *C23C 24/085* (2013.01); *C23C 24/103* (2013.01); *C23C 26/02* (2013.01); *B23K 2101/04* (2018.08); *B23K 2103/14* (2018.08)

(56) References Cited

U.S. PATENT DOCUMENTS

| | | |
|---|---|---|
| 4,698,237 A | 10/1987 | Macintyre |
| 5,290,368 A | 3/1994 | Gavigan et al. |
| 2008/0000881 A1 | 1/2008 | Storm et al. |
| 2010/0200123 A1 | 8/2010 | Kirkwood et al. |
| 2013/0260166 A1 | 10/2013 | Prichard et al. |
| 2015/0033561 A1 | 2/2015 | Bruck et al. |
| 2016/0375523 A1 | 12/2016 | Killian |

FOREIGN PATENT DOCUMENTS

| | | |
|---|---|---|
| CN | 104561995 A | 4/2015 |
| FR | 2698885 A1 | 6/1994 |
| JP | S5827971 A | 2/1983 |
| RU | 2522919 C1 | 7/2014 |
| WO | 2014012140 A1 | 1/2014 |
| WO | 2015086909 A1 | 6/2015 |

OTHER PUBLICATIONS

Hoche et al. "TiN-coating formation by pulsed ND:YAG laser irradiation of titanium in nitrogen" J. Coat. Technol. Res., vol. 5, No. 4, (2008), pp. 505-512.

Guo et al. "Microstructure and tribological properties of in situ synthesized TiN/Ti3Al intermetallic matrix composite coatings on titanium by laser cladding and laser nitriding." Materials Science and Engineering A. vol. 480 (2008), pp. 404-410.

Man et al. "In situ formation of a TiN/Ti metal matrix composite gradient coating on NiTi by laser cladding and nitriding." Surface & Coating Technology, vol. 200 (2006), pp. 4961-4966.

Tian et al. "Crack-Free Wear Resistance Coatings Produced on Pure Titanium and Ti—6Al—4V by laser nitriding." Surface Review and Letters, vol. 12, Nos. 5 & 6 (2005) pp. 741-744.

Zhongchao et al. "Laser induced films with high hardness and excellent wear- and corrosion-resistance" Published in Environmental and Energy Efficient Heat Treatment Technologies: Proceedings of the 4th International Seminar of International Federation for Heat Treatment and Surface Engineering. Beijing; China (Sep. 15-17, 1993). pp. 179-182.

Sibum. "Lasergaslegieren von Titanwerkstoffen. Entwicklung eines Verfahrens der Laserbehandlung von Titanwerkstoffen" "The alloying of titanium alloys by treating it with gas and laser. Development of an alloying process" Abschlussbericht.—English Abstract Only.

Kuzmych-Lanchuk et al. "Lase-Microplasma Reactive Powder Spraying of Titanium Coatings with Nitride Phases." Applied Mechanics and Materials, vol. 682, (2014), pp. 276-281.

Rozwadowska et al. "Wear resistance improvement of titanium bearings by laser gas nitriding." Advanced Materials Research, vols. 217-218, (2011), pp. 988-993.

Kot et al. "Analysis of the influence of sublayer thickness on the deformation mechanism and fracture of Ti/Tin Multilayer." Tribologia, vol. 41, No. 4 (2010), pp. 181-189.

Lima et al. "Microstructure and surface properties of laser-remelted titanium nitride coatings on titanium." Surface & Coatings Technology, vol. 199, (2005), pp. 83-91.

Cui et al. "Microstructure and wear performance of gradient Ti/TiN metal matrix composite coating synthesized using a gas nitriding technology." Surface and Coatings Technology, vol. 190, (2005), pp. 309-313.

Shigematsu et al. "Suface Hardening of Titanium with CO2 Laser." Hyomen Gijutsu. vol. 47, No. 9 (1996), pp. 808-809—English Abstract provided.

Matsuda et al., "Production of titanium-titanium nitride compositionally gradient coatings by laser spraying and their mechanical properties. VI. Friction and wear characteristics of laser spray coatings" Shikoku Kogyo Gijutsu Shikensho Kenkyu Hokoku vol. 25, (1993), pp. 96-109.—English Abstract provided.

Matsuda et al., "Production of titanium-titanium nitride compositionally gradient coatings by laser spraying and their mechanical properties. III. Formation of titanium-titanium nitride compositionally gradient films" Shikoku Kogyo Gijutsu Shikensho Kenkyu Hokoku, vol. 25, (1993) pp. 48-61.—English Abstract provided.

* cited by examiner

WEAR RESISTANT COATING

FIELD OF THE INVENTION

This invention relates to wear and galling resistant coatings. The invention has application to a broad range of abrasive environments, but has particular application to environments that are abrasive and corrosive.

BACKGROUND

In the course of extracting valuable minerals from a mined ore, the ore goes through a number of different processing stages. In the case of some nickel-containing ores, the preferred processing route involves high pressure acid leaching (HPAL) in autoclaves.

The ore is ground to provide a particle size that is suitable for processing and is then formed into a slurry by the addition of recycled process water. The slurry is supplied to an autoclave where sulfuric acid is added. The conditions in the autoclave are controlled depending on the mineralogy of the ore feed to maximize nickel leaching. However, processing conditions in the autoclave generally involve an elevated pressure in the range of 30 to 52 atm, temperatures in the range of 120° C. to 270° C. and acid addition of 200 to 500 kg/t of ore. Agitators are immersed in the hot acidic slurry to achieve suspension of solids.

In order to withstand these conditions, autoclaves are lined with titanium and the agitators are manufactured from titanium alloys but they are subject to considerable abrasion from contact with the slurry. Accordingly, agitators are subject to very abrasive and corrosive conditions and are typically manufactured with a wear resistant coating to improve the operational lifespan of the agitator.

The HPAL process operations are continuous. However, due to wear of agitators and other parts in an autoclave, periodic shutdowns are required to replace worn parts. Typically, this involves shutting down the autoclave for a period of about 3 weeks, including bringing the acid down in temperature and pressure, de-scaling, routine corrosion and wear monitoring, changing over agitators and re-commencing operations. Autoclaves are typically shut down every 9 months so that, amongst other factors, the wear of the agitators can be assessed. If the agitator blade has worn to an extent that agitator efficiency is adversely impacted, the agitator is replaced. If not, the agitator is placed back in service and wear is assessed again in a further 9 months.

Historically, agitators were not coated with a wear resistant coating. They were instead constructed of Grade 5 or Grade 12 titanium.

Wear resistant coatings of titanium dioxide ($TiO_2$) were adopted subsequently to improve the operational lifespan of the agitators. The titanium dioxide coating is applied by thermal spraying of $TiO_2$ particles directly onto an agitator. An example of a microstructure of a $TiO_2$ coating is shown in FIG. 1. The coating provides good wear resistance and it can be applied on-site at the autoclave. However, achieving a good coating requires a high level of preparation work to the agitator surface to ensure that it is free of contaminants. Even then, the $TiO_2$ coating forms a generally poor mechanical bond with the surface. Coating depth is limited to 0.5 mm because it is not possible to build up thicker layers of the coating due to inherent residual stresses within the coating. Due to properties of the $TiO_2$ coating, the coating must be totally removed from the agitator before a fresh coating is applied.

An alternative wear resistant, but not galling resistant, surface for agitators is reaction welded titanium nitride (typically a mixture of titanium and titanium/nitrogen intermetallics). An example of a microstructure of a titanium nitride hard-facing surface is shown in FIG. 2. This hard-facing is formed by producing a molten titanium weld pool on the surface of the agitator substrate and supplying a mixture of nitrogen and argon gas to the weld pool to cause a chemical reaction. As more nitrogen reacts with the titanium, the predominant phases produced change to higher nitrogen containing phases causing the coating to become brittle and porosity levels to increase. Due to the fact that this product is produced by an exothermic chemical reaction, and is limited by kinetic factors, the product is typically heterogeneous. The hardness of this product is not uniform since hardness is related to the diffusion of nitrogen through the molten titanium, which occurs at slower rates farther from the surface.

As shown in FIG. 2, the microstructure is a mixture of various titanium nitride intermetallics and a solid solution containing both titanium and dissolved nitrogen. The titanium nitride intermetallics are hard and provide the reacted surface with good wear resistant properties but poor galling resistant properties. With titanium nitride hard-facing, the reaction depth is generally around 1.5 mm. Additionally, the resultant reacted surface is metallurgically bonded to the substrate. While such bonding is beneficial for ensuring that the hard-facing remains on the agitator throughout the service life, the coating process involves consuming part of the agitator. This is problematic because it can change the tolerances of a product being coated and this can be critical to agitator efficiency. Furthermore, the hardness of the coating is off-set by an increase in brittleness that can lead to micro and macro cracking. Due to dilution of nitrogen into the titanium substrate to depths well below the visual reaction zone, titanium nitrided components are not typically re-nitrided because of the resultant reduction in mechanical properties of the base material.

There is a need for an improved wear resistant surface that is suitable for abrasive and corrosive conditions. It is advantageous for the surface to be able to be reapplied easily without damage to the component.

SUMMARY OF THE DISCLOSURE

The applicant has recognized that titanium nitride (TiN) has beneficial properties that make it suitable to form a wear resistant & galling resistant coating for abrasive and corrosive environments. Specifically, TiN has a Vickers hardness of 2400 (which is harder than the nickel-containing ore) and, importantly, it has a specific gravity that is slightly greater than titanium. This means that there is only a slight tendency for TiN particles to sink in a hopper containing titanium particles and titanium based alloys, and will not sink quickly in molten titanium alloys.

The applicant has further recognized that coatings of TiN can be formed by incorporating particles of TiN generally in a solid state into a molten matrix material of titanium or titanium alloy. Effectively, solid TiN particles are embedded in a commercially pure titanium alloy matrix. The high hardness of the TiN particles imparts high wear resistance and the commercially pure titanium matrix imparts corrosion resistance and ductility. By adjusting the hardness of the matrix by way of dissolving more of the TiN particle, it has been discovered that the galling can be reduced or anti-galling properties increased. Accordingly, the invention provides in one aspect a feed for forming a wear resistant coating on a substrate by a welding process that heats the feed and the substrate, wherein:

(a) 35 to 50 wt % of the feed comprises particles of titanium nitride; and (b) a balance of the feed comprises particles of commercially pure titanium or titanium alloy and incidental impurities.

The feed may comprise titanium nitride particles in the range of 35 to 45 wt %. Optionally, the feed may comprise titanium nitride particles in the range of 35 to 42 wt %.

The titanium nitride and the commercially pure titanium or titanium alloy may be in the form of particles.

The size of particles in the feed is limited by practical aspects of particle feeders. It is anticipated, however, that particles sizes up to 250 μm are suitable and, indeed, even larger particle sizes may be used in the feed. Particle size selection is subject to competing factors of small particles having poor flow properties and of small particles requiring less heat input to cause melting. For this reason, the titanium or titanium alloy particles may have a particle size that is less than the size of the titanium nitride particles. In one embodiment, the titanium nitride particles have a particle size in the range of 5 to 170 μm. The titanium or titanium alloy particles may have a size in the range of 20 to 170 μm.

The small particle size means that considerably less energy is required to heat the titanium alloy particles to their melting point to form molten titanium alloy.

However, the TiN particles predominantly remain solid during the process. A small fraction of the nitride particles dissolve in the molten titanium alloy which form secondary titanium nitrides upon cooling and a small proportion of nitrogen that remains dissolved in the matrix having a small hardening effect. A sufficient gas shield, typically argon, is provided during welding so that oxygen and other contaminants do not affect the weld.

Below 35 wt % titanium nitride particles, the volume of titanium nitride particles in the coating drops off to an extent that the commercially pure titanium alloy matrix becomes excessively exposed to the wear environment and, therefore, the wear and galling resistance of the coating decreases. Additionally, there is an increase in the extent to which titanium nitride particles will dissolve in the commercially pure titanium alloy matrix such that the nitrogen content of the matrix increases, thereby causing a larger volume of secondary titanium nitrides to form. These secondary titanium nitrides are less beneficial to large particle abrasion and galling resistance but are useful for providing erosion resistance from process fluid flow.

Above 50 wt % titanium nitride particles, the coating becomes difficult to weld because the stresses created upon solidification are spread over a smaller volume of matrix formed by commercially pure titanium or titanium alloy. This increase in stress per unit volume leads to cracking of the overlay.

The feed may further comprise an inert conveying gas for entraining the particles and for providing an inert shield to a weld pool formed by the welding process before the weld pool solidifies. Optionally, the gas may be argon.

The titanium alloy particles may comprise alloying elements with the balance being at least 50% titanium and incidental impurities.

In accordance with another aspect, there is provided a method of forming a coating on a substrate of titanium alloy, the coating being resistant to wear and galling in a corrosive and abrasive environment, the method comprising the steps of:

(a) delivering a feed according to the first aspect to a surface of the substrate by conveying the feed to the substrate in an inert conveying gas and controlling the flow of the conveying gas to control the feed rate of the feed;

(b) heating the feed and the substrate to cause at least the commercially pure titanium or titanium alloy particles, at least some of the titanium nitride particles and at least the exposed surface of the substrate to melt to form a melt pool;

whereby, on solidification of the melt pool, at least some of the titanium nitride particles are embedded in a matrix formed from the melt pool, thereby forming a wear resistant and galling resistant coating on the substrate.

This aspect is based on the realisation that, by controlling the heat input to the substrate and the feed, it is possible to control the microstructure of the coating so that it includes a matrix that comprises a solid solution of titanium and nitrogen, includes titanium nitride particles from the feed and one or more precipitated titanium nitride phases. It follows that the method can be controlled to provide the coating with a range of properties tailored for specific applications. Heat input to the feed and the substrate may include preheating of the substrate before steps (a) and (b) to a temperature above ambient temperature and may include exposure to a targeted energy source to cause localised heating of the substrate and the feed. In the case of the targeted energy source, the heat input may be adjusted by adjusting intensity and duration of exposure to the targeted energy source and by adjusting the area of substrate exposed to the targeted energy source.

The substrate preheat temperature may be in a range of 50° C. to 150° C. The substrate may be maintained at that the preheat temperature throughout the method. If the preheat temperature exceeds this range, the total heat input is such that the volume of secondary nitrides that precipitate upon solidification of the melt pool can cause cracking in the coating. Optionally, the substrate preheat temperature may be maintained in a range of 50° C. to 100° C. The preheat temperature range is limited to this range to account for exothermic reactions that occur in the weld pool. That is, the heat generated by the exothermic reactions contributes heat to the weld pool and, therefore, affects the temperature of the weld pool and the time that the weld pool takes to solidify. If the time for solidification is too long, secondary nitrides may form in significant volumes that result in cracking and porosity in the coating. The limited and relatively low preheat temperature range is selected to reduce or avoid the cracking and porosity in the coating caused by the secondary nitrides.

Multiple phases of titanium nitride may be formed according to the process. In particular, the titanium nitride may be deposited on a substrate with a range of hardness which can be controlled to produce coatings that have high resistance to galling and high wear resistance. More specifically, it is believed that controlling the temperature of the molten material and the time during which the molten material remains molten enables the hardness of the wear resistant coating to the controlled.

In line with this belief, the method may further comprise controlling the temperature of the molten material to be between the melting temperature of titanium nitride and the vaporisation temperature of titanium.

This temperature control is an important aspect because the reaction between titanium and nitrogen is highly exothermic. This means that there is a risk that the extra heat generated in the process could result in the molten materials exceeding the vaporisation temperature of titanium. If this occurs, porosity will form throughout the wear-resistant coating.

Further in line with this belief, the method may comprise controlling phases of titanium nitride formed upon solidification of the molten materials by controlling the time that the molten material remains molten.

The method may further involve controlling conditions to form the wear resistant and galling resistant coating with a matrix of titanium nitride having a hardness in the range of 400 Hv to 550 Hv.

The hardness of the matrix affects the susceptibility of the wear resistant coating to galling. In particular, the higher matrix hardness contributes to a reduction in susceptibility to galling. However, in contrast to titanium carbide, which has a higher hardness than titanium nitride, the matrix of titanium nitride is harder than the matrix of the wear resistant coating formed with titanium carbide. It is believed that the higher hardness is attributable to the higher content of nitrogen in the matrix as a result of a lower melting temperature of titanium nitride particles compared to the melting temperature of titanium carbide. The selection of a softer material to form a harder matrix and more wear resistant coating is, therefore, counter-intuitive.

Step (a) may involve conveying the feed to the substrate in an inert conveying gas and controlling the flow of the conveying gas to control the feed rate of the feed.

The method may involve depositing one or more layers of the wear resistant coating on the substrate to build up the thickness of the wear resistant coating.

Titanium has a high affinity for oxygen and, as a result, a titanium alloy substrate will have an oxide surface layer. Many techniques for coating a titanium substrate involve removing the oxide layer (for example, such as grit blasting or baking the substrate) in an inert atmosphere. Another option involves removing the contaminated surface layer from the substrate, for example by chipping the surface layer off the substrate. This may involve milling. Sufficient bonding is generated without oxide removal between coatings formed according to the method, but bonding is improved when the oxidized layer is removed. The method may further comprise carrying out steps (a) and (b) while the substrate is exposed to the ambient atmosphere. In other words, it is not a requirement of the method to be carried out in an inert environment to avoid exposure of the coating and substrate to oxygen in the ambient atmosphere.

The method may further comprise a step of pre-treating the substrate to remove contaminants. The pre-treating step may be carried out while the substrate is in contact with the ambient atmosphere.

The surface pre-treatment step is selected to remove oxygen, iron and other contaminants from the surface. In one form, the pre-treatment step involves chipping the substrate with a tungsten carbide burr to remove contaminants. Such chipping may be performed in the presence of the ambient atmosphere, i.e. in the presence of oxygen.

Steps (a) and (b) may be provided by a welding technique. Such welding techniques include laser cladding, TIG welding, MIG welding and PTA welding.

In a further aspect, there is provided a titanium alloy autoclave or valve component having a coating that is resistant to wear in a corrosive and abrasive environment, wherein the wear and galling resistant coating comprises particles of titanium nitride dispersed in a matrix of commercially pure titanium or titanium alloy. The titanium alloy may comprise alloying elements with the balance being at least 50% titanium and incidental impurities.

The coating may be metallurgically bonded to the substrate. Additionally, such bonding may occur during application of the wear and galling resistant coating on the substrate.

The titanium nitride particle size may be in the range of 20 to 170 μm.

The titanium nitride particles may comprise 35 to 45 wt % of the wear resistant coating. Optionally, the titanium nitride particles may comprise 35 to 42 wt % of the wear resistant coating.

It also has the benefit over titanium dioxide coatings in that it is metallurgically bonded and can be applied to a greater thickness. It is expected to provide coated substrates with a longer service life due to the improved wear and galling resistance rates. However, corrosion becomes an important consideration when the service life of a component is extended, such as in an autoclave that processes nickel-containing ore. It will be appreciated that the corrosion resistant properties of titanium will sustain the service condition of the coated substrate in the corrosive conditions.

The wear resistant coating may be formed to a thickness of greater than 0 to 2 mm. Optionally, the coating may be formed to a thickness of greater than 0 to 4 mm. Further optionally, the coating may be formed to a thickness of up to 10 mm.

BRIEF DESCRIPTION OF THE DRAWINGS

An embodiment of the invention will now be described, by way of example only, with reference to the accompanying drawings, in which.

DETAILED DESCRIPTION

The description that follows is in the context of applying a wear resistant coating to a substrate of titanium alloy. It is important to appreciate, however, that the wear resistant coating may be applied to other materials that can be directly welded with titanium and other alloys by use of a suitable butter layer.

Figure 5:
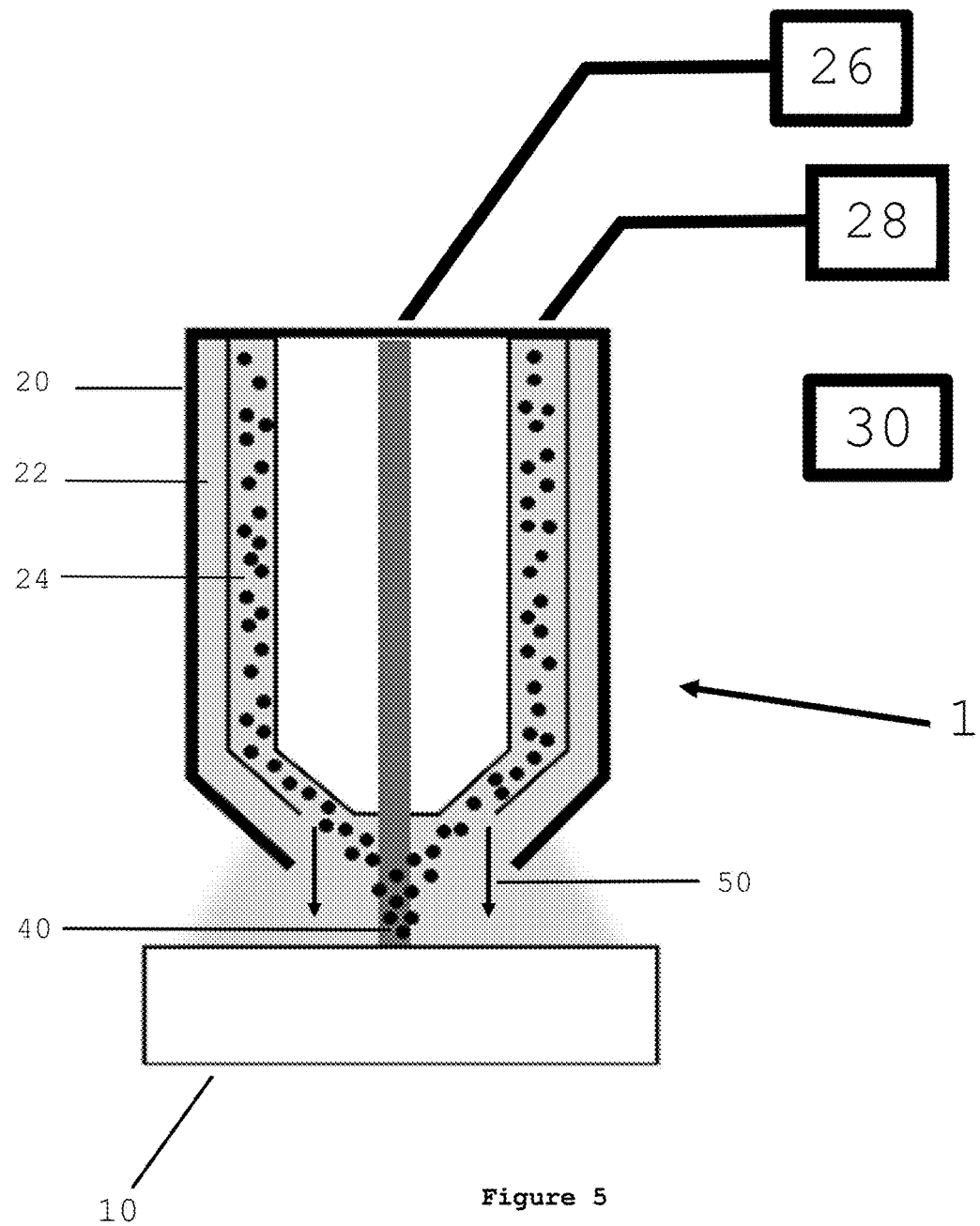
FIG. 5 is a schematic representation of an apparatus for forming a wear resistant coating.

An apparatus 1 for forming a wear resistant coating on a substrate 10 is shown in FIG. 5.

The apparatus 1 comprises a spray nozzle 20 having an elongate body. The spray nozzle 20 includes a laser generator 22 that generates a laser 40. The laser generator 22 is aligned along a central longitudinal axis of the elongate body. A sleeve surrounds the laser generator 22 to form an annular feed flow chamber 24.

The laser generator is linked to a power source 26 to generate the laser 40 with sufficient energy to melt small particles of titanium in the range of 20 to 170 μm. The chamber 24 is linked via a conduit to a reservoir 28 of feed particles for forming the wear resistant coating. The reservoir 28 is supplied with argon gas from a gas source 30 to fluidize the particles and convey the entrained particles through the conduit and chamber 24 and then onto the substrate 10.

The flow of particles and gas from the chamber 24 is controlled to converge from the annular opening surrounding the laser generator 22 in a flow stream (denoted by an arrow marked 50 in FIG. 5) that intersects the laser 40 at the surface of the substrate 10. Accordingly, the feed particles are subject to high temperatures at the surface of the substrate 10.

The feed particles comprise a blend of titanium alloy particles and titanium nitride particles. The titanium nitride particles comprise 35 to 50 wt % of the blend. Both the titanium particles and the titanium nitride particles have a size in the range of 20 to 170 µm.

It will be appreciated that alternative configurations for supplying feed particles to the surface of the substrate 10 may be adopted. For example, the titanium alloy particles and the titanium nitride particles may be supplied from separate reservoirs and combined together in the chamber 24 so that a blend of feed particles is formed in the chamber 24 and is supplied as described above to the surface of the substrate 10.

Alternatively, the blend of particles may be formed at the surface of the substrate 10 by supplying the titanium alloy particles and the titanium nitride particles through separate nozzles that direct the particles to the point on the surface of the substrate 10 that is irradiated by the laser.

The applicant has observed that, although the laser melts the titanium alloy particles, the titanium nitride particles generally remain in a solid state and become embedded in the wear resistant coating by being surrounded in a matrix of titanium alloy dispersed with secondary titanium nitrides.

The applicant has also observed that because the laser energy is selected to melt the titanium alloy particles only, a weld pool generated by the laser quenches so rapidly under the argon shield gas (powder gas) that oxygen is unable to react with the molten titanium. This results in a wear resistant coating that is generally free of oxygen.

| Substrate: | Titanium grade 12 |
| --- | --- |
| Substrate thickness: | >25 mm |
| Preheat: | >50° C./<150° C. |
| Ti particles: | Amperit 155.093 |
| Ti particle size/density: | 90 to 125 µm/4.51 g/cm$^3$ |
| Ti particle weight %: | 58 |
| TiN particles: | Amperit K80 |
| TiN particle size/density: | 40 to 145 µm/5.22 g/cm$^3$ |
| TiN particle weight %: | 42 |
| Substrate pre-cleaning: | acetone wash |
| Conveying gas and flow rate: | Argon at 10 l/min |
| Shielding gas & flow rate: | Argon at 23 l/min |
| Ti/TiN particle feed rate: | 18 g/min |
| Laser: | Laserline LDF 6,000-100 |
| Spot size: | 8.5 mm |

Figure 1:
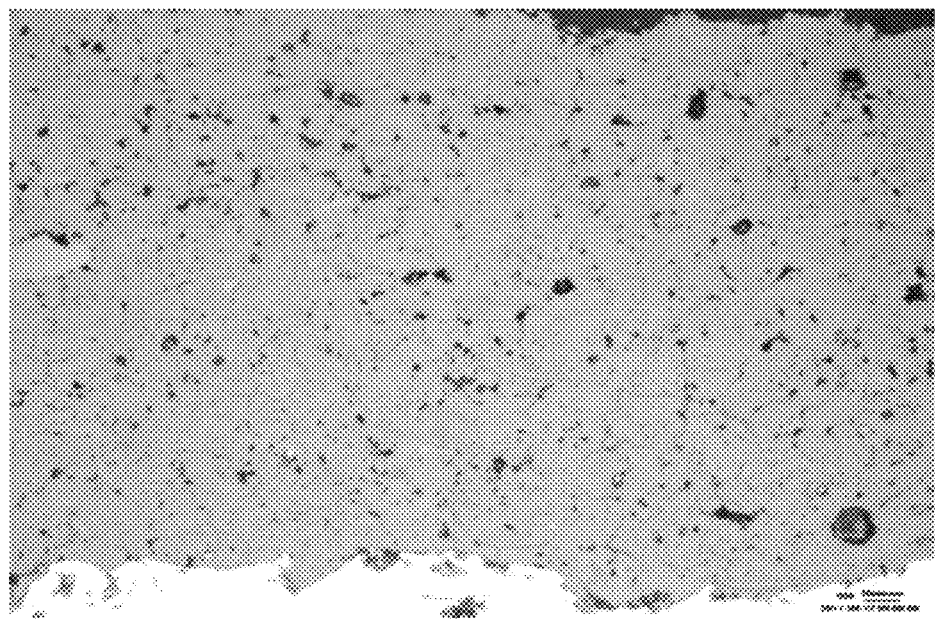
FIG. 1 is a cross-section showing the microstructure of a $TiO_2$ wear resistant coating.
Figure 2:
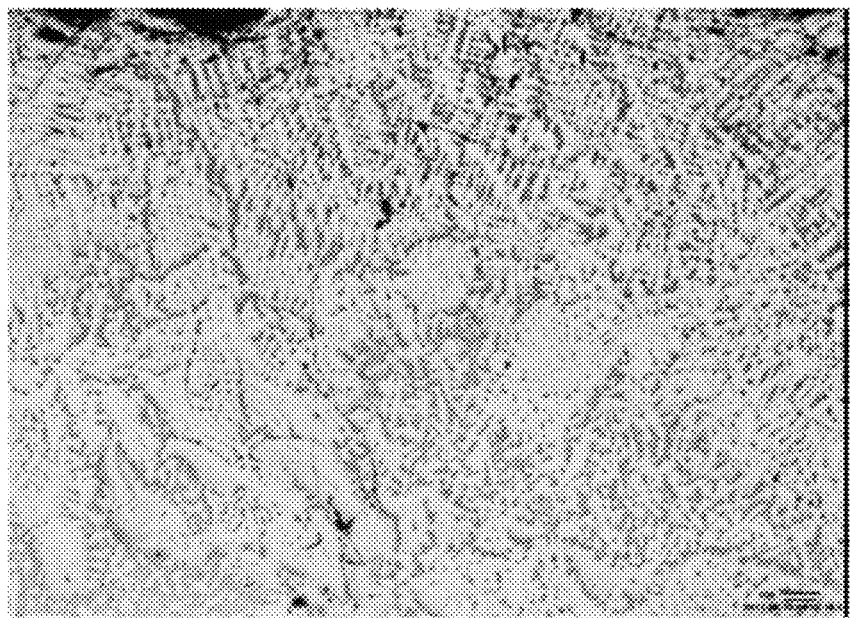
FIG. 2 is a cross-section showing the microstructure of a TiN wear resistant coating.
Figure 3:
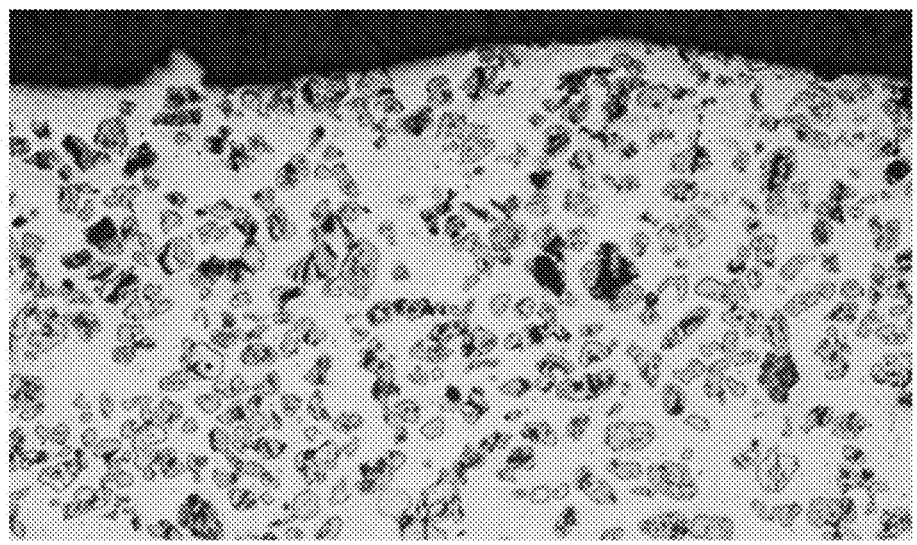
FIG. 3 is a cross-section showing an embodiment of a microstructure of a TiN wear resistant coating formed according to the invention.
Figure 4:
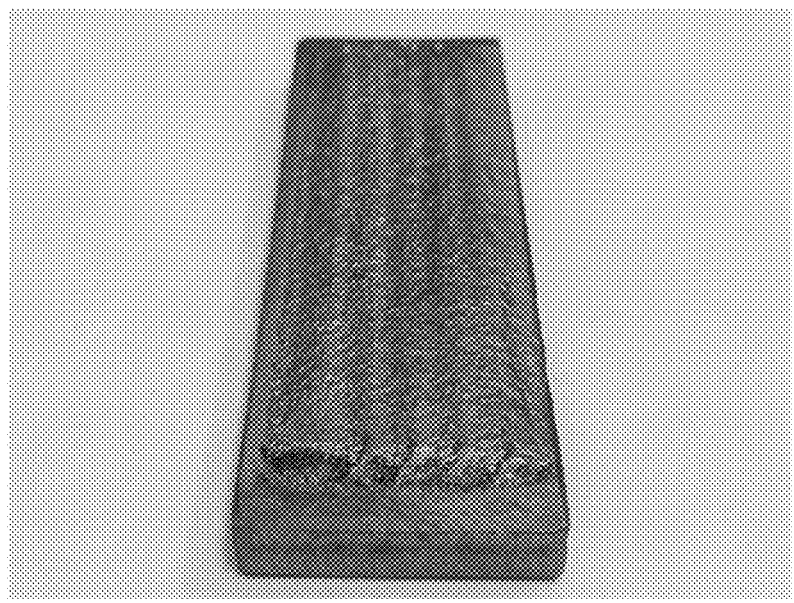
FIG. 4 is a perspective view of overlapping sections of the wear resistant coating in FIG. 3 formed on the surface of a titanium substrate.

An example of a microstructure for a wear resistant coating formed in accordance with these conditions is shown in FIG. 3. Discrete particles of titanium nitride are shown dispersed generally homogenously in a generally continuous matrix of titanium alloy with secondary precipitates of titanium nitrides. These secondary precipitates add both wear & galling resistance. The titanium alloy of the substrate is metallurgically bonded with the wear resistant coating. A wear resistant coating formed by a series of side-by-side laser passes is shown in FIG. 4. The feed rate of particles identified above produces a wear resistant coating thickness of 1.0 mm. However, it is possible with this process to build up the thickness of the coating by running subsequent laser passes and feed particles over already formed coating. In this manner, it is possible to build up the coating to any desired depth, but it is expected that thicknesses of up to 10 mm will be suitable for a wide variety of applications. For example, the wear resistant coating may be applied to agitator blades for autoclaves, diffuser cones, wear plates and valve components.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

It will be understood to persons skilled in the art of the invention that many modifications may be made without departing from the spirit and scope of the invention.

It is to be understood that, if any prior art publication is referred to herein, such reference does not constitute an admission that the publication forms a part of the common general knowledge in the art, in Australia or any other country.

In addition, the foregoing describes only some embodiments of the invention(s), and alterations, modifications, additions and/or changes can be made thereto without departing from the scope and spirit of the disclosed embodiments, the embodiments being illustrative and not restrictive.

Furthermore, invention(s) have been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention(s). Also, the various embodiments described above may be implemented in conjunction with other embodiments, for example, aspects of one embodiment may be combined with aspects of another embodiment to realize yet other embodiments.

The invention claimed is:

1. A method of forming a coating on a substrate of titanium alloy, the coating being resistant to wear and galling in a corrosive and abrasive environment, the method comprising the steps of:
   (a) delivering a feed to a localized surface of a substrate by conveying the feed to the substrate in an inert conveying gas and controlling the flow of the conveying gas to control the feed rate of the feed, the feed consisting of:
      (i) 35 to 50 wt % titanium nitride particles;
      (ii) a balance of commercially pure titanium or titanium alloy particles with incidental impurities; and
   (b) heating the feed and the substrate to cause the commercially pure titanium or titanium alloy particles, at least some of the titanium nitride particles and the localized surface of the substrate to melt to form a melt pool;
   whereby, on solidification of the melt pool, at least some of the titanium nitride particles are embedded in a matrix formed from melt pool, thereby forming a wear resistant and galling resistant coating on the substrate.

2. The method defined in claim 1, wherein the substrate is a component of an autoclave.

3. The method defined in claim 2, wherein the autoclave component is an agitator.

4. The method defined in claim 1, wherein the corrosive and abrasive environment comprises autoclave processing conditions that extract valuable minerals from a mined ore.

5. The method defined in claim 4, wherein the corrosive and abrasive environment comprises autoclave processing conditions involving an elevated pressure in the range of 30 to 52 atm, temperatures in the range of 120° C. to 270° C. and acid addition to a slurry of ground ore and water of 200 to 500 kg/t of ore.

6. A method as defined in claim 1, wherein the method involves depositing one or more layers of the wear resistant coating on the substrate to build up the thickness of the wear resistant coating.

7. A method as defined in claim 1, wherein the method further comprises carrying out steps (a) and (b) while the substrate is exposed to the ambient atmosphere.

8. A method as defined in claim 1, wherein the method further comprises a step of pre-treating the substrate to remove contaminants.

9. A method as defined in claim 8, wherein the pre-treating step is carried out while the substrate is in contact with the ambient atmosphere.

10. A method as defined in claim 8, wherein the surface pretreatment step is selected to remove oxygen, iron and other contamination.

11. A method as defined in claim 8, wherein the pretreatment step involves removing a contaminated surface layer from the substrate.

12. A method as defined in claim 1, wherein the method further comprises controlling the temperature of the molten material to be between the melting temperature of titanium and the vaporisation temperature of titanium.

13. A method as defined in claim 1, wherein the method comprises controlling phases of titanium nitride formed upon solidification of the molten materials by controlling the time that the molten material remains molten.

14. A method as defined in claim 1, wherein the method includes preheating the substrate before steps (a) and (b) and maintaining the substrate temperature in a range of 50° C. to 150° C.

15. A method as defined in claim 1, wherein the method further comprises controlling conditions to form the wear resistant and galling resistant coating with a matrix of titanium nitride having a hardness in the range of 400 Hv to 550 Hv.

* * * * *